United States Patent [19]

Bremanis et al.

[11] Patent Number: 5,017,611

[45] Date of Patent: May 21, 1991

[54] ETHYL-3-(2-ETHYL-2,2-DIMETHYLHY-DRAZINIUM)-PROPIONATE SALTS TO TREAT ARRHYTHMIA

[76] Inventors: Gunar A. Bremanis, ulitsa 1905 goda, 18, Jurmala; Felix Z. Meerson, ulitsa Svobodv, 95, kv. 149, Moscow; Ivars Y. Kalvinsh, ulitsa Miera, 17, kv. 8, Salaspils; Nurlan Abdikaliev, ulitsa Dzhambula, 66, kv. 22, Alma-Ata; Petr T. Trapentsier, ulitsa F. Engelsa, 40, kv. 24, Riga; Ma/Ya G. Pshennikova, Panfilovsky pereulok, 5, kv. 42, Moscow; Irene B. Antsena, ulitsa A. Deglava, 106/3, kv. 16, Riga; Edmund Y. Lukevits, ulitsa Ierikju, 43, kv. 10, Riga; Boris Z. Simkhovich, ulitsa Avotu, 4, kv. 57, Riga, all of U.S.S.R.

[21] Appl. No.: 428,901

[22] Filed: Oct. 30, 1989

Related U.S. Application Data

[62] Division of Ser. No. 170,557, Mar. 21, 1988, abandoned.

[30] Foreign Application Priority Data

Mar. 25, 1987 [SU] U.S.S.R. ............................. 4217356

[51] Int. Cl.$^5$ ............................................. A61K 31/22
[52] U.S. Cl. ..................................................... 514/551
[58] Field of Search ......................................... 514/551

[56] References Cited

U.S. PATENT DOCUMENTS 4,451,485 5/1984 Kalvinsh et al. ..................... 514/554
4,704,403 3/1987 Bremanis et al. .................... 514/554

FOREIGN PATENT DOCUMENTS 2140013 11/1984 United Kingdom ............... 514/551

*Primary Examiner*—Stanley J. Friedman
*Assistant Examiner*—Diane Gardner
*Attorney, Agent, or Firm*—Burgess, Ryan and Wayne

[57] ABSTRACT

The present invention relates to the art of organic chemistry. The novel compounds - ethyl-3-(2-ethyl-2,2-dimethylhydrazinium)-propionate salts have the general formula:

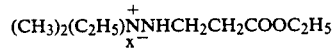

$$(CH_3)_2(C_2H_5)\overset{+}{N}NHCH_2CH_2COOC_2H_5 \quad X^-$$

wherein X is Cl, Br, I.

The compounds of the present invention possess an antiarrhythmic effect.

2 Claims, No Drawings

ETHYL-3-(2-ETHYL-2,2-DIMETHYLHYDRAZINIUM)-PROPIONATE SALTS TO TREAT ARRHYTHMIA

This is a division of application Ser. No. 170,557, filed Mar. 21, 1988.

FIELD OF APPLICATION OF THE INVENTION

The present invention relates to the art of organic chemistry, namely to novel compounds - ethyl-3-(2-ethyl-2,2-dimethylhydrazinium)-propionate salts possessing an antiarrhythmic effect which can be useful in medicine as active ingredients of pharmaceutical preparations.

BACKGROUND OF THE INVENTION

Known in the art are 3-(2,2,2-trisubstituted hydrazinium)-propionates possessing both hypotensive and antiarrhythmic activity (U.S. Pat. No. 4,633,014).

The closest prior art compound in respect of its chemical structure is 3-(2,2,2-trimethylhydrazinium)-propionate (quaterine) possessing an antiarrhythmic effect (U.S. Pat. No. 4,451,485).

However, 3-(2,2,2-trimethylhydrazinium)-propionate similarly to 3-(2,2,2-trisubstituted hydrazinium)-propionates is effective on models of toxic arrhythmiae, whereas under the conditions of cardiological clinics toxic arrhythmiae are encountered rather rarely, while actually originating arrhythmiae are the result of a combined effect of stresses, ischemia, reoxygenation, cardiosclerosis. In experiments on models of toxic arrhythmiae, 3-(2,2,2-trimethylhydrazinium)-propionate decreases the frequency of occurrence of arrhythmiae and heart fibrillation, but the effect is observed as a result of a 10-days' administration which, when applied to a human being, corresponds to a considerably longer period of time. Furthermore, the antiarrhythmic effect of this compound was manifested only in the form of a preventive effect in the case of acute ischemia. Its effect in the case of reoxygenation arrhythmiae, as well as post-infarction cardiosclerosis, has not been studied.

This preparation has found no application in medicine as an antiarrhythmic agent.

The compounds according to the present invention, viz. ethyl-3-(2-ethyl-2,2-dimethylhydrazinium)-propionate salts are novel and hitherto unknown in the literature.

SUMMARY OF THE INVENTION

It is an object of the present invention to provide novel compounds displaying activity in respect of ischemic arrhythmiae and arrhythmiae caused by post-infarction cardiosclerosis.

This object is accomplished by providing, according to the present invention, novel compounds, viz. ethyl-3-(2-ethyl-2,2-dimethylhydrazinium)-propionate salts of the general formula:

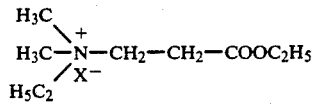

wherein X is Cl, I, Br.

The compounds according to the present invention are colourless crystalline substances well soluble in water, alcohols, chloroform, and insoluble in non-polar solvents. The m.p. is 73° to 112° C. The structure of the compounds according to the present invention has been proven by the data of elemental analysis and PMR spectrography.

DETAILED DESCRIPTION OF THE INVENTION

The compounds according to the present invention possess an antiarrhythmic activity which has been studied in experiments on animals.

The antiarrhythmic effect of the compounds according to the present invention has been studied in succession on two models. The former model utilized rats of the Vistar line under Nembutal narcosis (50 mg/kg, intraperitoneally) under conditions of open thorax and artificial pulmonary ventilation wherein an electrocardiogram was recorded and the electric threshold of the heart fibrillation was determined by the method described hereinbelow and then an acute myocardial ischemia was simulated by ligation of the left coronary artery. 4-6 minutes after the creation of ischemia the electrical threshold of the heart fibrillation was measured again. Later on, within the period of 7-10 min of ischemia a progressive cardiac rhythm disturbance ranging from extrasystoles to ventricular tachycardia and fibrillation. The duration of these arrhythmiae was measured in seconds. Then the coronary occlusion was removed and in this manner the phenomenon of reperfusion (reoxygenation) of the myocardium was reproduced. In response thereto, so-called reperfusion arrhythmiae occurred the duration of which was also measured in seconds. In these experiments, the effect of the compounds according to the present invention on the ischemic depression of the heart fibrillation threshold, as well as on the severity of ischemic and reperfusion arrhythmiae was evaluated.

The second model utilized rats of the Vistar line wherein an experimental myocardial infarction was created according to Sellier, i.e. by way of ligation of the left coronary artery and, 1.5 months thereafter, at a pronounced post-infarction cardiosclerosis and presence of a dense connective-tissue cicatrix of a more than 100 mg mass, the electrical threshold of the heart fibrillation and its ectopic activity were determined. For the determination of the electrical threshold of the heart fibrillation, thoracotomy was performed and, by means of a stimulator energized from the R wave of the electrocardiogram the heart was irritated by untimely single pulses of 10 ms duration through a coaxial electrode intramurally introduced into the right ventricle. By way of scanning, the R-T range with three-threshold pulses the beginning of the relative refractory period was found, i.e. the moment at which a single response occurred in reaction to the irritation. The time from the wave R to this point was considered as the effective refractory period. The value of the threshold of fibrillation of ventricles was assessed as a minimum current force in mA at which fibrillation took place. In these experiments, the current force that caused fibrillation was recorded simultaneously with the electrocardiogram and the arterial pressure in the carotid artery.

In the determination of the ectopic activity of the heart, its response to irritation of the vagus nerve was assessed. In so doing, the right vagus nerve in the neck was isolated and its peripheral end was irritated using platinum electrodes (duration—2 ms, delay—5 ms, frequency—20 Hz) by means of an electrostimulator. After the determination of the threshold current force equal to 0.3–0.4 mA, the response to irritation was successively evaluated with the interval of 5 min the irritation value being equal to 1, 2, 3 and 4 threshold values. In these experiments, the electrocardiogram was taken and arterial pressure in the carotid artery was recorded by means of an electric pressure gauge.

For a comparative assessment of the arrhythmic activity of the compounds according to the present invention on all models of arrhythmiae, the antiarrhythmic effect of a close chemical analog—quaterine and a known antiarrhythmic preparation—lidocain was studied.

The compound according to the present invention, viz. ethyl-3-(2,2-dimethyl-2-ethylhydrazinium)-propionate iodide was administered per os in the sole dose of 25 mg/kg two hours before the experiment. Quaterine was administered in a similar manner, but in the dose of 100 mg/kg; lidocain was administered in the dose of 5 mg/kg which is usually employed in clinics for arresting arrhythmia, 5 min before the coronary occlusion or before the acute experiment.

The test results are shown in Tables 1–3 hereinbelow.

The data shown in Tables 1 to 3 demonstrate the results of the first stage of the studies. In this stage the effect of the above-mentioned compound according to the present invention, quaterine and lidocain on the ischemic depression of the fibrillation threshold and pronouncedness of ischemic and reperfusion arrhythmiae was studied.

TABLE 1

Effect of the compound according to the present invention, viz. ethyl-3-(2,2-dinethyl-2-ethylhydrazinium)-propionate iodide on the fibrillation threshold of ventricles and heart rhythm disturbances in ischemia and reperfusion

| Groups of animals (15 animals in each) | Initial heart beat rate, beat/min | Initial electrical threshold of ventricular fibrillation, mA | Ischemia Electrical threshold of ventricular fibrillation on the 4–6th minute | Ventricular extrasystole, total duration, s | Ventricular tachycardia, total duration, s | Fibrillation. Total duration, s | Total duration of arrhythmiae, s | Reperfusion Ventricular extrasystole. Total duration, s | Ventricular tachycardia. total duration, s | Fibrillation. Total duration s | ration of ration of miae, s miae, s |
|---|---|---|---|---|---|---|---|---|---|---|---|
| 1 | 2 | 3 | 4 | 5 | 6 | 7 | 8 | 9 | 10 | 11 | 12 |
| Control | 403 ± 6 | 6.0 ± 0.3 | 1.0 ± 0.1 | 176 | 354 (3)* | 405 | 935 | 174 | 574 | 347 | 1095 |
| Compounds of this invention | 400 ± 6.7 | 7.0 ± 0.5 | 2.5 ± 0.2 | 175 (2)* | 189 (6)* | 5 | 369 | 67 | 349 | 149 | 565 |
| Statistical certainty of differences between the control and test groups | P > 0.5 | P > 0.5 | P < 0.01 | | | | | | | | |

Note. In brackets with the sign* indicated is the number of animals in the group wih the specified rhythm disturbances.

TABLE 2

Effect of quaterine on the threshod of fibriation of the heart ventricles and heart rhythm disturbances in ischemia and reperfusion (m ± m and M)

| Groups of animals (15 animals in each) | Initial heart beat rate, beat/min | Initial electrical threshold of ventricular fibrillation, mA | Ischemia Electrical threshold of ventricular fibrillation on the 4–6th minute | Ventricular extrasystole, total duration, s | Ventricular tachycardia, total duration, s | Fibrillation. Total duration, s | Total duration of arrhythmiae, s | Reperfusion Ventricular extrasystole. Total duration, s | Ventricular tachycardia. total duration, s | Fibrillation. Total duration s | ration of ration of miae, s miae, s |
|---|---|---|---|---|---|---|---|---|---|---|---|
| 1 | 2 | 3 | 4 | 5 | 6 | 7 | 8 | 9 | 10 | 11 | 12 |
| Control | 310 ± 12 | 7.0 ± 0.6 | 1.2 ± 0.1 | 168 | 303 | 350 | 820 | 221 | 458 | 430 | 1109 |
| Quaterine | 340 ± 15 | 4.8 ± 0.8 | 1.5 ± 0.1 | 206 | 370 | 411 | 987 | 230 | 425 | 438 | 1103 |
| Statistical certainty of differences between the control and test groups $P_{1-2}$ | >0.5 | <0.05 | >0.5 | | | | | | | | |

TABLE 3

Effect of lidocain on the threshold of fibrilation of the heart ventricles and heart rhythm disturbances in ischemia and reperfusion

| Groups of animals (15 animals in each) 1 | Initial heart beat rate, beat/min 2 | Initial electrical threshold of ventricular fibrillation, mA 3 | Ischemia | | | | | Reperfusion | | | |
|---|---|---|---|---|---|---|---|---|---|---|---|
| | | | Electrical threshold of ventricular fibrillation on the 4–6th minute 4 | Ventricular extrasystole, total duration, s 5 | Ventricular tachycardia, total duration, s 6 | Fibrillation. Total duration, s 7 | Total duration of arrhythmiae, s 8 | Ventricular extrasystole. Total duration, s 9 | Ventricular tachycardia. total duration s 10 | Fibrillation. Total duration s 11 | ration of ration of miae, s miae, s 12 |
| Control | 403 ± 6 | 6.0 ± 0.1 | 1.0 ± 0.1 | 176 | 354 | 405 | 935 | 174 | 574 | 347 | 1095 |
| Lidocain | 395 ± 8.3 | 7.1 ± 0.5 | 1.3 ± 0.3 | 175 | 300 | 375 | 850 | 153 | 498 | 351 | 902 |
| Statistical certainty of differences between the control and test groups | P > 0.5 | P > 0.5 | P > 0.5 | | | | | | | | |

The data shown in Table 1 make it possible to assess the antiarrhythmic effect of the above-mentioned compound according to the present invention. As it is seen from this Table, an acute myocardial ischemia caused by coronary occlusion results in a many-time fall of the fibrillation threshold in the control animals already within 4–6 min the threshold current force necessary to cause fibrillation is 1 mA, not 6 mA as in the initial state. On the 6–10th minutes of ischemia a growing rhythm disorder is developing—from extrasystoles and ventricular tachycardia to fibrillation. The total duration of these arrhythmiae for the control animals, as it is seen from Table 1, is slightly shorter than 1,000 s, the fibrillation taking 405 s. In other words, an acute cardiac ischemia in these experiments, likewise in experiments carried out by other researchers, results, at the beginning, in a many-time drop of the fibrillation threshold, i.e. in a higher "preparedness" of the heart to arrhythmiae, and then—in the development of arrhythmiae and fibrillation per se. It also follows from the data of Table 1 that after the elimination of the coronary occlusion—during the period of reperfusion—the heart rhythm disturbances do not disappear and, in some cases, can even be aggravated and, as a result, the total duration of arrhythmiae over 5 min of reperfusion becomes the same as in the case of ischemia, i.e. exceeds 1,000 s.

Therefore, we have had the opportunity for observing severe ischemic and reperfusion arrhythmiae and to evaluate them quantitatively. As it is further seen from the data of Table 1, a preliminary administration of the compound according to the present invention in the above-specified dose substantially prevents the heart disturbances discussed hereinabove and usually originating in the case of ischemia and myocardial reperfusion. This preparation substantially prevents the ischemic depression of the fibrillation threshold: while in the control the threshold decreased under the effect of ischemia by six times, in the animals administered with the compound according to the present invention this drops was by 2.5 times less. Under the influence of the compound according to the present invention, the phenomena of fibrillation of the heart were substantially completely prevented and the total duration of arrhythmiae in the case of ischemia was reduced by three times. A similar effect was demonstrated by the compound according to the present invention in the case of reperfusion arrhythmia. It should be noted that the compound according to the present invention reduced the occurrence of the heart fibrillation by more than two times and nearly twice reduces the total duration of arrhythmiae in the case of reperfusion.

The data shown in Table 2 illustrate the effect of the second studied preparation—quaterine which has the structure most close to that of the compound according to the present invention. As it is seen from Table 2, an acute myocardial ischemia and the subsequent reperfusion in these experiments have resulted in the control animals in the same disturbances of the heart rhythm that were obtained in the previous study in the control animals and described hereinabove (Table 1). This demonstrates the stability of the employed model and experiment conditions. At the same time, the data of Table 2 show that a preliminary administration, prior to coronary occlusion, of quaterine in a dose equivalent to the dose of the compound according to the present invention produced substantially no effect on the origination and character of ischemic and reperfusion arrhythmiae.

Shown in Table 3 are the data illustrating the effect of a preliminary administration of a known antiarrhythmic preparation—lidocain—on the threshold of fibrillation, pronouncedness of ischemic and reperfusion arrhythmiae under conditions of an acute experiment. It follows from the data of this Table that this known preparation of the antiarrhythmic effect shows substantially no preventive influence on said arrhythmiae. This is in correspondence with the known showing data that lidocain is effective only for arresting arrhythmiae, but it has no preventive effect. Therefore, the studies for evaluation of the antiarrhythmic effect of the compound according to the present invention, quaterine and lidocain on a model of ischemic and reperfusion arrhythmiae show that the compound according to the present invention displays a pronounced antiarrhythmic effect, both in the case of ischemic and reperfusion arrhythmiae. Quaterine and lidocain do not possess a similar effect.

Also studied was the effect produced by the preparations according to the present invention on the disturbance of the heart electrical stability and its ectopic activity in the case of a post-infarction cardiosclerosis, i.e. under conditions where these preparations were administered not for prevention, but for elimination of disorders of the electrical stability of the heart. Such experimental therapy was conducted under conditions of the absence of stress and of an acute ischemia. The results of the tests are shown in Tables 4 through 6 hereinbelow.

The data shown in Table 4 illustrate the antiarrhythmic effect of the compound according to the present invention in the case of post-infarction cardiosclerosis; they were obtained on animals employed in experiments 1.5 months after the induction of the left ventricle infarction. The determination of the electrical threshold of the heart fibrillation and its ectropic activity were carried out using the above-described method. As it is shown in Table 4, post-infarction cardiosclerosis, providing no substantial influence on the negative chronotropic effect of the vagus nerve, results in a considerable reduction of the fibrillation threshold, i.e. in an increased "preparedness" of the heart to arrhythmiae; it also results in the appearance of rhythm disorders in the form of extrasystole under conditions of stimulation of the vagus nerve: the fibrillation threshold in the case of cardiosclerosis becomes reduced by 2.8 times as compared with the control, the total number of extrasystoles appearing against the background of stimulation of vagus nerve is 401, whereas in the intact animals no rhythm disturbances are observed under the same conditions. As it is also seen from Table 4, the compound according to the present invention to a considerable extent removes the above-mentioned disturbances in the electrical stability of the heart. It is seen that under the effect of the preparation of this invention the threshold of the heart fibrillation is increased to a value which does not differ with statistical certainty from the control value, while the total number of extrasystoles is decreased by 5 times. Therefore, the compound according to the present invention provides an essential antiarrhythmic effect in the case of post-infarctional cardiosclerosis.

The data shown in Table 5 demonstrate the results of studies for evaluation of the antiarrhythmic effect of quaterine in the case of post-infarctional cardiosclerosis. They point to similarity of values of the characteristics obtained in this study for the control animals and the animals with cardiosclerosis to the values of the characteristics obtained in corresponding groups of the animals employed in the previous study wherein the effect of the compound according to the present invention was evaluated. This proves the stability of the model of the post-infarctional cardiosclerosis and conditions of the experiment in these studies. At the same time, as it also follows from the data of Table 5, quaterine administered in the dose equivalent to the dose of the compound according to the present invention provides no protective therapeutic effect in the case of a disturbed electrical stability of the heart in post-infarctional cardiosclerosis, i.e. it has shown no antiarrhythmic effect.

The data of Table 6 reflect the results of the experiments, wherein the effect of the antiarrhythmic preparation—lidocain—on disturbances of the electrical stability of the heart was evaluated in the case of post-infarctional cardiosclerosis. It is seen that lidocain did not remove the disturbances of electrical stability, of the heart, i.e. its "preparedness" to arrhythmiae which, as it has been already mentioned hereinbefore, corresponds to the general idea of the effect produced by this preparation.

Therefore, the compound according to the present invention when administered perorally in a single non-toxic dose displays a clearly pronounced antiarrhythmic effect in ischemic arrhythmiae, reperfusion arrhythmiae; it also eliminates the disturbances of the electrical stability of the heart, i.e. its "preparedness" to arrhythmiae in post-infarctional cardiosclerosis. Quaterine and lidocain, upon the same mode of administration in an equivalent dosage, do not possess a preventive antiarrhythmic effect in the case of ischemia and reperfusion; neither they remove the disturbances of the heart electrical stability in the case of post-infarctional cardiosclerosis. On the basis of the tests thus performed, it has been found out that the compounds according to the present invention possess a clearly pronounced antiarrhythmic effect at a single-time oral administration in the case of ischemic and reoxygenational arrhythmiae and can be useful in clinics for prevention and elimination of already shaped disturbances of the electrical stability of the heart, i.e. its "preparedness" to arrhythmiae, in post-infarctional cardiosclerosis.

The compounds according to the present invention are low-toxic ones. Upon an intraperitoneal administration to white mice the $LD_{50}$ of ethyl-3-(2,2-dimethyl-2-ethylhydrazinium)-propionate iodide is 145 mg/kg, the $LD_{50}$ of ethyl-3-(2,2-dimethyl-2-ethylhydrazinium)-propionate bromide is 120 mg/kg, and $LD_{50}$ of ethyl-3-(2,2-dimethyl-2-ethylhydrazinium)-propionate chloride is 120 mg/kg.

TABLE 4

Effect of the compound according to the present invention on the threshold of ventricular fibrillation and ectopic heart activity in post-infarctional cardiosclerosis (M ± m and M)

| No. of the group of animals 1 | Groups of animals 2 | Initial heart beat rate, beat/min 3 | Threshold voltage upon stimulation of vagus nerve, V 4 | Value of reduction of the heart beat rate under the effect of stimulation of vagus nerve, beat/min | | | | Threshold of ventricular fibrillation, mA 9 | Total number of extrasystoles in vagus bradycardia 10 |
|---|---|---|---|---|---|---|---|---|---|
| | | | | 1 threshold 5 | 2 thresholds 6 | 3 thresholds 7 | 4 thresholds 8 | | |
| 1 | Control (10 animals) | 398 ± 12 | 0.23 ± 0.002 | 56 ± 4 | 158 ± 16 | 176 ± 16 | 200 ± 16 | 5.8 ± 0.4 | — |
| 2 | Compound of the present invention (8 animals) | 412 ± 9 | 0.40 ± 0.100 | 54 ± 5 | 129 ± 22 | 147 ± 21 | 161 ± 17 | 5.8 ± C.4 | — |
| 3 | Cardiosclerosis (9 animals) | 383 ± 8 | 0.28 ± 0.05 | 47 ± 6.7 | 144 ± 20 | 174 ± 22 | 209 ± 21 | 2.1 ± 0.2 | 401 |
| 4 | Cardioslerosis + the compound of the present | 352 ± 8 | 0.25 ± 0.03 | 40 ± 8 | 99 ± 25 | 116 ± 24 | 124 ± 27 | 4.3 ± 0.5 | 81 |

TABLE 4-continued

Effect of the compound according to the present invention on the threshold of ventricular fibrillation and ectopic heart activity in post-infarctional cardiosclerosis (M ± m and M)

| No. of the group of animals 1 | Groups of animals 2 | Initial heart beat rate, beat/min 3 | Threshold voltage upon stimulation of vagus nerve, V 4 | Value of reduction of the heart beat rate under the effect of stimulation of vagus nerve, beat/min | | | | Threshold of ventricular fibrillation, mA 9 | Total number of extrasystoles in vagus bradycardia 10 |
|---|---|---|---|---|---|---|---|---|---|
| | | | | 1 threshold 5 | 2 thresholds 6 | 3 thresholds 7 | 4 thresholds 8 | | |
| | invention (9 animals) | | | | | | | | |

Statistical certainty of differences between groups
No 1 and No 2 $P_{1-2} > 0.05 > 0.05$
No 1 and No 3 $P_{1-3} > 0.05 < 0.001$
No 3 and No 4 $P_{3-4} < 0.05 < 0.001$
No 1 and No 4 $P_{1-4} > 0.05 > 0.05$

TABLE 5

Effect of quaterine on the threshold of ventricular fibrillation and ectopic hear activity in post-infarctional cardiosclerosis

| No. of the group of animals 1 | Groups of animals 2 | Initial heart beat rate, beat/min 3 | Threshold voltage upon stimulation of vagus nerve, V 4 | Value of reduction of the heart beat rate under the effect of stimulation of vagus nerve, beat/min | | | | Threshold of ventricular fibrillation mA 9 | Total number of extrasystoles in vagus bradycardia 10 |
|---|---|---|---|---|---|---|---|---|---|
| | | | | 1 threshold 5 | 2 thresholds 6 | 3 thresholds 7 | 4 thresholds 8 | | |
| 1 | Control (10 animals) | 400 ± 14 | 0.26 ± 0.002 | 52 ± 5 | 141 ± 14 | 173 ± 15 | 198 ± 19 | 6.4 ± 0.5 | — |
| 2 | Quaterine (9 animals) | 409 ± 11 | 0.30 ± 0.004 | 56 ± 4 | 150 ± 17 | 166 ± 16 | 205 ± 21 | 6.1 ± 0.6 | — |
| 3 | Cardiosclerosis (9 animals) | 395 ± 10 | 0.32 ± 0.03 | 45 ± 5 | 147 ± 16 | 170 ± 20 | 210 ± 18 | 2.3 ± 0.2 | 487 |
| 4 | Cardiosclerosis + quaterine (9 animals) | 390 ± 12 | 0.25 ± 0.003 | 48 ± 6 | 152 ± 19 | 181 ± 21 | 200 ± 23 | 2.5 ± 0.4 | 343 |

Statistical certainty of differences between groups
No 1 and No 2 $P_{1-2} > 0.05 > 0.05$
No 1 and No 3 $P_{1-3} > 0.05 < 0.001$
No 3 and No 4 $P_{3-4} > 0.05 > 0.05$
No 1 and No 4 $P_{1-4} > 0.05 < 0.001$

TABLE 6

Effect of lidocain on the threshold of ventricular fibrillation and ectopic activity of the heart in post-infarctional cardiosclerosis

| No. of the group of animals 1 | Groups of animals 2 | Initial heart beat rate, beat/min 3 | Threshold voltage upon stimulation of vagus nerve, V 4 | Value of reduction of the heart beat rate under the effect of stimulation of vagus nerve, beat/min | | | | Threshold of ventricular fibrillation, mA 9 | Total number of extrasystoles in vagus bradycardia 10 |
|---|---|---|---|---|---|---|---|---|---|
| | | | | 1 threshold 5 | 2 thresholds 6 | 3 thresholds 7 | 4 thresholds 8 | | |
| 1 | Control (10 animals) | 398 ± 12 | 0.23 ± 0.002 | 56 ±]5 | 158 ± 16 | 176 ± 16 | 200 ± 16 | 5.8 ± 0.4 | — |
| 2 | Lidocain (8 animals) | 400 ± 8 | 0.20 ± 0.05 | 54 ± 5 | 142 ± 12 | 160 ± 13 | 160 ± 15 | 6.2 ± 0.5 | — |
| 3 | Cardiosclerosis (9 animals) | 383 ± 15 | 0.28 ± 0.05 | 47 ± 6 | 144 ± 20 | 174 ± 22 | 209 ± 21 | 2.1 ± 0.2 | 401 |
| 4 | Cardiosclerosis + lidocain (9 animals) | 370 ± 20 | 0.25 ± 0.04 | 49 ± 6 | 156 ± 18 | 179 ± 20 | 200 ± 23 | 2.6 ± 0.4 | 367 |

Statistical certainty of differences between groups
No 1 and No 2 $P_{1-2} > 0.05 > 0.05$
No 1 and No 3 $P_{1-3} > 0.05 < 0.001$
No 3 and No 4 $P_{3-4} > 0.05 > 0.05$
No 1 and No 4 $P_{1-4} > 0.05 < 0.001$ The compounds according to the present invention, viz. ethyl-3-(2,2-dimethyl-2-ethylhydrazinium)-propionate salts are prepared by alkylation of a known compound - ethyl-3-(2,2-dimethylhydrazinium)-propionate by means of ethylhalides in absolute ethanol in an inert atmosphere at the solvent boiling temperature for 10 hours, or by way of changing the halo-anion from ethyl-3-(2,2-dimethyl-2-ethylhydrazinium)-propionate iodide by passing an aqueous solution of the latter through an anion-exchange resin in its chloride or bromide form respectively.

For a better understanding of the present invention, some specific examples illustrating the method for preparing the compounds of this invention are given hereinbelow.

EXAMPLE 1

To a solution of 87 g (0.54 mol) of ethyl-3-(2,2-dimethylhydrazino)-propionate in 400 ml of absolute ethanol 94 g (0.6 mol) of ethyl iodide are added. The resulting mixture is heated on a water bath in the atmosphere of nitrogen for 10 hours. The solvent is evaporated under a reduced pressure. After treatment with acetone a precipitate is formed which is filtered-off and washed with acetone. Crystallization is effected from a mixture ethanol-acetone. The yield of the desired product - ethyl-3-(2,2-dimethyl-2-ethylhydrazinium)-propionate iodide is 142 g (83.2%), melting point is 110°–112° C.

Found, %: C 34.50, H 6.85, N 9.05. $C_9H_{21}H_2O_2J$. Calculated, %: C 34.19, H 6.69, N 8.86.

The PMR spectrum (in $CDCl_3$): δ1.28 (t, 3H, $OCH_2\underline{CH_3}$); 1.45 (t, 3H, $N^+CH_2\underline{CH_3}$); 2.67 (t, 2H, $\underline{CH_2}COOC_2H_5$); 3.24 (dt, 2H, $\underline{CH_2}NH$); 3.57 (s, 6H, $\overline{N^+(CH_3)_2}$); 3.81 (q, 2H, $N^+\underline{CH_2}CH_3$); 4.14 (q, 2H, $O\underline{CH_2}CH_3$); 6.64 ppm (t, 1H, $\overline{NH}$).

EXAMPLE 2

The process is conducted in a manner similar to that described in the foregoing Example 1. The desired product is crystallized from a mixture ethanol—acetone. The yield of the desired product - ethyl-3-(2,2-dimethyl-2-ethylhydrazinium)-propionate bromide is 90.5%, the melting point is 108.5° C.

Found, %: C 40.35, H 7.25, N 10.70. $C_9H_{21}N_2O_2Br$. Calculated, %: C 40.16, H 7.05, N 10.41.

The PMR spectrum (in $CDCl_3$): δ1.26 (t, 3H, $OCH_2\underline{CH_3}$); 1.43 (t, 3H, $N^+CH_2\underline{CH_3}$); 2.66 (t, 2H, $\underline{CH_2}COOC_2H_5$); 3.22 (dt, 2H, $\underline{CH_2}NH$); 3.52 (s, 6H, $\overline{N^+(CH_3)_2}$; 3.79 (q, 2H, $N^+\underline{CH_2}CH_3$); 4.13 (q, 2H, $O\underline{CH_2}CH_3$); 7.19 ppm (t, 1H, $\overline{NH}$).

EXAMPLE 3

A solution of 19.5 g (62 mmol) of ethyl-3-(2,2-dimethyl-2-ethylhydrazinium)-propionate iodide in 100 ml of water is passed through a strongly basic ion-exchange resin IRA-400 (in the form of chloride-ion). Elution is effected with water. The combined aqueous solution is evaporated under a reduced pressure. The residue is crystallized from acetone.

The yield of the desired product is 11.8 g (89.9%) - ethyl-3-(2,2-dimethyl-2-ethylhydrazinium)-propionate chloride. M.p. 73°–74° C.

Found, %: C 45.36, H 10.05, N 13.32, $C_9H_{21}N_2O_2Cl$. Calculated, %: C 45.17, H 9.95, N 13.17.

The PMR spectrum (in $CDCl_3$): δ1.26 (t. 3H, $OCH_2\underline{CH_3}$); 1.43 (t, 3H, $N^+CH_2\underline{CH_3}$); 2.62 (t, 2H, $\underline{CH_2}COOC_2H_5$); 3.18 (t, 2H, $\underline{CH_2}\overline{NH}$); 3.53 (s, 6H, $\overline{N^+(CH_3)_2}$): 3.82 (q, 2H, $N^+\underline{CH_2}CH_3$); 4.14 (q, 2H, $O\underline{CH_2}CH_3$); 7.4 ppm (s, 1H, $\overline{NH}$).

What is claimed is:

1. A method of prophylaxis and treatment of arrhythmias in ischaemia, reperfusion and postinfarction cardiosclerosis, in a host which comprises administering to said host an effective amount of a compound selected from the group consisting of ethyl-3-(2-ethyl-2,2-dimethylhydrazinium) propionate chloride, ethyl-3-(2-ethyl-2,2-dimethylhydrazinium) propionate bromide and ethyl-3-(2-ethyl-2,2-dimethylhydrazinium) propionate iodide.

2. The method of claim 6 wherein said effective amount is 25 mg/kg.

* * * * *